United States Patent
Youk et al.

(10) Patent No.: US 11,939,278 B2
(45) Date of Patent: Mar. 26, 2024

(54) METHOD OF PRODUCING OLIGOMER

(71) Applicant: LG CHEM, LTD., Seoul (KR)

(72) Inventors: Kyung Seog Youk, Daejeon (KR); Min Ho Sun, Daejeon (KR); Jong Hun Song, Daejeon (KR); Hong Min Lee, Daejeon (KR); Moon Sub Hwang, Daejeon (KR); Jeong Seok Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/777,962

(22) PCT Filed: Sep. 6, 2021

(86) PCT No.: PCT/KR2021/012030
§ 371 (c)(1),
(2) Date: May 18, 2022

(87) PCT Pub. No.: WO2022/050788
PCT Pub. Date: Mar. 10, 2022

(65) Prior Publication Data
US 2023/0183148 A1  Jun. 15, 2023

(30) Foreign Application Priority Data

Sep. 7, 2020 (KR) .................... 10-2020-0113695
Aug. 30, 2021 (KR) .................... 10-2021-0114794

(51) Int. Cl.
*C07C 2/06* (2006.01)
*C07C 7/00* (2006.01)
(Continued)

(52) U.S. Cl.
CPC .............. *C07C 2/06* (2013.01); *C07C 7/005* (2013.01); *C07C 7/08* (2013.01); *C07C 7/14883* (2013.01)

(58) Field of Classification Search
CPC .. C07C 2/06; C07C 7/005; C07C 7/08; C07C 7/14883; C07C 2531/22; C07C 2/26; C07C 7/09
See application file for complete search history.

(56) References Cited

U.S. PATENT DOCUMENTS

| 2008/0177012 A1 | 7/2008 | Penzo et al. |
| 2015/0203418 A1 | 7/2015 | Meiswinkel et al. |
| 2018/0237360 A1 | 8/2018 | Han |

FOREIGN PATENT DOCUMENTS

| CN | 107074679 A | 8/2017 |
| CN | 107207382 A | 9/2017 |

(Continued)

*Primary Examiner* — Thuan D Dang
(74) *Attorney, Agent, or Firm* — Bryan Cave Leighton Paisner LLP

(57) ABSTRACT

Provided is a method of producing an oligomer, the method including: supplying a monomer stream and a solvent stream to a reactor to perform an oligomerization reaction to produce a reaction product; supplying a discharge stream of the reactor to a separation device, and supplying an upper discharge stream of the separation device including an unreacted monomer to the reactor and supplying a lower discharge stream of the separation device to a settling tank; settling a polymer in the settling tank and removing the polymer, and supplying the lower discharge stream of the separation device from which the polymer is removed to a high-boiling point separation column; removing a high-boiling point material from a lower discharge stream of the high-boiling point separation column and supplying an upper discharge stream of the high-boiling point separation column including an oligomer to a solvent separation column; and separating a solvent and the oligomer in the solvent separation column.

10 Claims, 2 Drawing Sheets

(51) Int. Cl.
*C07C 7/08* (2006.01)
*C07C 7/148* (2006.01)

(56) References Cited

FOREIGN PATENT DOCUMENTS

| | | | |
|---|---|---|---|
| EP | 0 397 273 | A | 11/1990 |
| JP | 2009-120588 | A | 6/2009 |
| JP | 2015-527311 | A | 9/2015 |
| JP | 2016-65051 | A | 4/2016 |
| JP | 2018-502088 | A | 1/2018 |
| JP | 2022-521320 | A | 4/2022 |
| KR | 10-0433971 | B1 | 5/2004 |
| KR | 10-2007-0116221 | A | 12/2007 |
| KR | 10-2014-0005115 | A | 1/2014 |
| KR | 10-2017-0028203 | A | 3/2017 |
| KR | 10-2017-0045547 | A | 4/2017 |
| KR | 10-2017-0058935 | A | 5/2017 |
| KR | 10-2017-0098282 | A | 8/2017 |
| KR | 10-2018-0006327 | A | 1/2018 |
| WO | 2011/112184 | A1 | 9/2011 |
| WO | 2016-105226 | A | 6/2016 |
| WO | 2016/152591 | A1 | 9/2016 |
| WO | 2020-171730 | A | 8/2020 |

【FIG. 1】
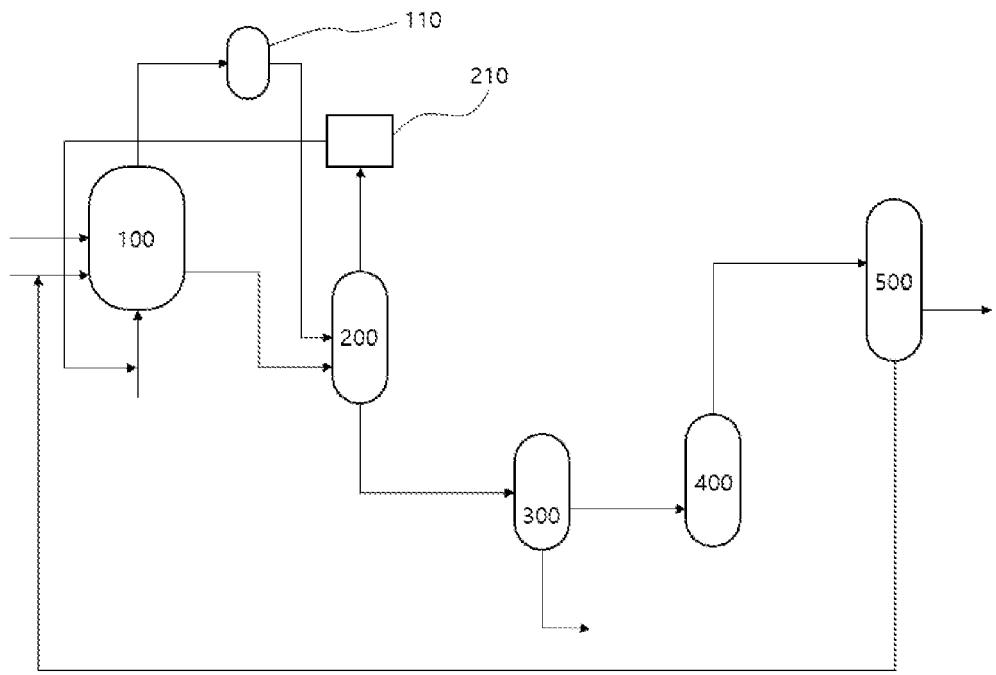
【FIG. 2】
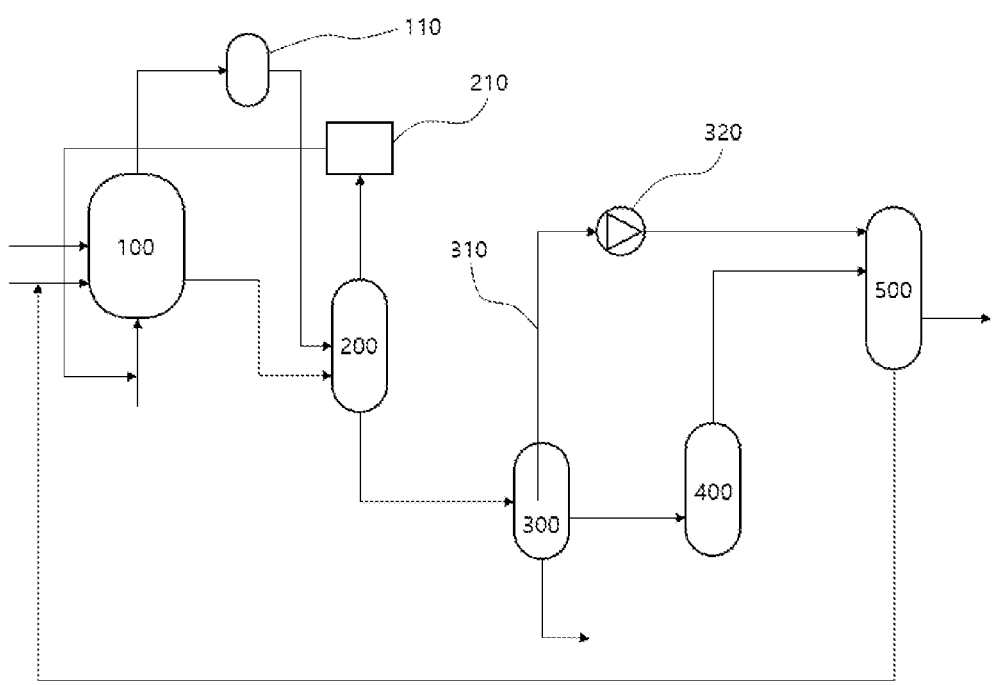

【FIG. 3】
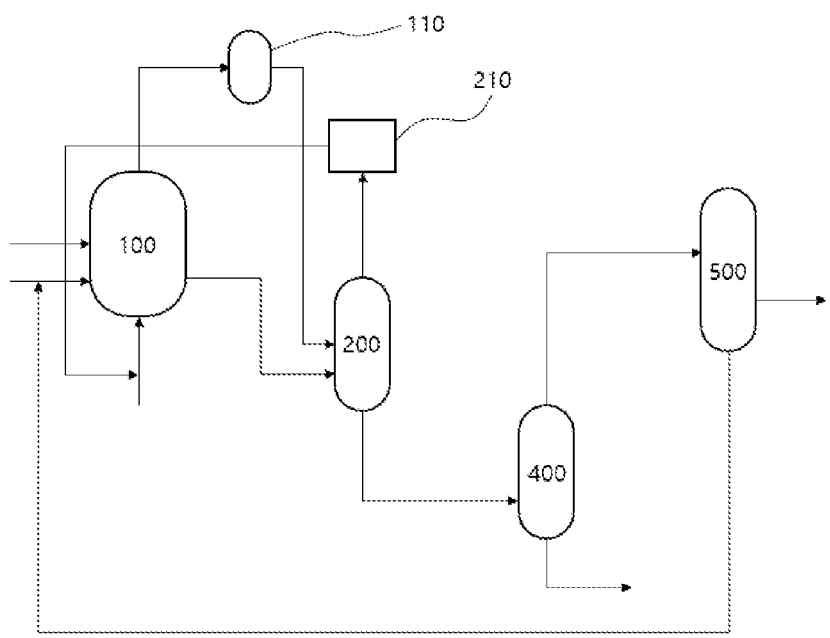

METHOD OF PRODUCING OLIGOMER

CROSS-REFERENCE TO RELATED APPLICATIONS

The present application is a National Phase entry pursuant to 35 U.S.C. § 371 of International Application No. PCT/KR2021/012030, filed on Sep. 6, 2021, and claims the benefit of and priority to Korean Patent Application No. 10-2020-0113695, filed on Sep. 7, 2020 and Korean Patent Application No. 10-2021-0114794, filed on Aug. 30, 2021, the entire contents of which are incorporated by reference in their entirety for all purposes as if fully set forth herein.

TECHNICAL FIELD

The present invention relates to a method of producing an oligomer, and more particularly, to an efficient method of producing an oligomer, for removing polymer by-products produced with lower energy costs and facilitating a reuse of a solvent in oligomer production.

BACKGROUND ART

An α-olefin (alpha-olefin) is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The α-olefins such as 1-hexene and 1-octene are produced representatively by an oligomerization reaction of ethylene. The ethylene oligomerization reaction is carried out by an oligomerization reaction (trimerization reaction or tetramerization reaction) of ethylene in the presence of a catalyst using ethylene as a reactant, and the reaction product produced by the reaction includes not only a multi-component hydrocarbon mixture including 1-hexene and 1-octene to be desired but also a small amount of polymer as a by-product during catalysis and the polymer floats in a liquid reaction medium in a reactor, which causes a problem in that the polymer accumulates to a certain thickness due to a fouling phenomenon in a reactor as time passes. In this case, since operation of the reactor should be shut down, there is a problem of increased costs required in a washing process as well as a problem of decreased production due to a decreased operation time.

In this regard, a high-boiling point separation column and a solvent separation column should be provided for removing a polymer in the reaction product and recovering the solvent used in a large amount as compared with the reactant to be reused. Here, as the content of the polymer in a stream supplied to the high-boiling point separation column and a solvent separation column is higher, energy costs and time for separation are increased.

DISCLOSURE

Technical Problem

An object of the present invention is to provide a method for reducing energy costs and shortening a separation time in removing a polymer floating in a reaction product during a process of producing an oligomer, recovering and reusing a solvent, and separating the oligomer with a high purity, in order to solve the problems mentioned in Background Art.

Technical Solution

In one general aspect, a method of producing an oligomer includes: supplying a monomer stream and a solvent stream to a reactor to perform an oligomerization reaction to produce a reaction product; supplying a discharge stream of the reactor to a separation device, and supplying an upper discharge stream of the separation device including an unreacted monomer to the reactor and supplying a lower discharge stream of the separation device to a settling tank; settling a polymer in the settling tank and removing the polymer, and supplying the lower discharge stream of the separation device from which the polymer is removed to a high-boiling point separation column; removing a high-boiling point material from a lower discharge stream of the high-boiling point separation column and supplying an upper discharge stream of the high-boiling point separation column including an oligomer to a solvent separation column; and separating a solvent and the oligomer in the solvent separation column.

Advantageous Effects

According to the method of producing an oligomer of the present invention, a reaction product produced by an oligomerization reaction in a reactor is supplied to a settling tank before being supplied to a high-boiling point separation column and a solvent separation column, thereby removing a polymer included in the reaction product to lower a content of a polymer in a stream supplied to the high-boiling point separation column and the solvent separation column, so that a time for separation may be shortened and also energy cost may be reduced.

In addition, in the present invention, an upper layer liquid stream having a high content of a solvent in the settling tank is directly supplied to a solvent separation column without passing through the high-boiling point separation column, thereby decreasing a flow rate of a stream supplied to the high-boiling point separation column to further decrease an energy use in the high-boiling point separation column.

DESCRIPTION OF DRAWINGS

FIGS. 1 and 2 are process flow diagrams of a method of producing an oligomer according to an exemplary embodiment of the present invention, respectively.

FIG. 3 is a process flow diagram of a method of producing an oligomer according to the Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a fluid flow in the process, or may refer to the fluid itself flowing in a moving line (pipe). Specifically, the "stream" may refer to both a fluid itself flowing in a pipe connecting each device and a fluid flow. In addition, the fluid may refer to a gas or a liquid.

Hereinafter, the present invention will be described in more detail for better understanding of the present invention, with reference to the following FIG. 1 and FIG. 2.

According to the present invention, a method of producing an oligomer is provided. As the method of producing an oligomer, there is provided a method of producing oligomer including: supplying a monomer stream and a solvent stream to a reactor 100 to perform an oligomerization reaction to produce a reaction product; supplying a discharge stream of the reactor 100 to a separation device 200, and supplying an upper discharge stream of the separation device including an unreacted monomer to the reactor 100 and supplying a lower discharge stream of the separation device to a settling tank 300; settling a polymer in the settling tank 300 and removing the polymer, and supplying the lower discharge stream of the separation device from which the polymer is removed to a high-boiling point separation column 400; removing a high-boiling point material from a lower discharge stream of the high-boiling point separation column 400 and supplying an upper discharge stream of the high-boiling point separation column 400 including an oligomer to a solvent separation column 500; and separating a solvent and the oligomer in the solvent separation column 500.

According to an exemplary embodiment of the present invention, a monomer stream and a solvent stream may be supplied to a reactor 100 to perform an oligomerization reaction to produce a reaction product.

The reactor 100 may be for oligomerizing a monomer in the presence of a catalyst and a solvent to produce an oligomer. Thus, an oligomer product may be continuously produced.

In addition, the monomer may include ethylene. Specifically, a monomer stream including an ethylene monomer may be supplied to the reactor 100 to produce an α-olefin as a desired oligomer by an oligomerization reaction. Here, the oligomerization reaction is carried out in a reaction medium in a lower or a middle area of the reactor 100, and the oligomerization reaction of the monomer may be carried out in a state of a liquid state dissolved in a solvent, in the presence of a catalyst and a cocatalyst. The oligomerization reaction may refer to a reaction in which a monomer is oligomerized. The oligomerization may be referred to as trimerization or tetramerization depending on the number of monomers to be polymerized, and these are collectively called multimerization.

The α-olefin, which is an important material, used in copolymers, cleaning agents, lubricants, plasticizers, and the like, is commercially widely used, and in particular, 1-hexene and 1-octene are often used as a comonomer for adjusting the density of polyethylene in the production of linear low-density polyethylene (LLDPE). The α-olefin such as 1-hexene and 1-octene may be produced by for example, a trimerization reaction or tetramerization reaction of ethylene.

The oligomerization reaction of the monomer may be carried out by a homogeneous liquid phase reaction, a slurry reaction of which the catalyst is in the form of being partially not dissolved or not dissolved at all, a two-phase liquid/liquid reaction, or a bulk phase reaction or gas phase reaction of which the product acts as a main medium, in the presence or absence of a solvent, by applying the reaction system and a common contact technology.

The catalyst may include a transition metal source. The transition metal source may be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafloro-2,4-pentanedionate, chromium (III) acetatehydroxide, chromium (III) acetate, chromium (III) butyrate, chromium (III) pentanoate, chromium (III) laurate, and chromium (III) stearate.

The cocatalyst may include, for example, one or more selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, modified methylaluminoxane, and borate.

As such, in the process of oligomerizing a monomer in the presence of a catalyst and a solvent, a polymer such as polyethylene may be produced as a by-product, in addition to an oligomer product. The polymer floats in a liquid reaction medium in the reactor 100, and as time passes, a problem in which the polymer is accumulated in the reactor 100 to a certain thickness due to a fouling phenomenon arises. In this case, since operation of the reactor 100 should be shut down, there are a problem of increased costs required in a washing process as well as a problem of decreased production due to a decreased operation time.

In addition, a high-boiling point separation column 400 and a solvent separation column 500 should be provided for removing a polymer in the reaction product, and recovering and reusing a solvent used in a large amount as compared with a reactant. Here, as the content of the polymer in a stream supplied to the high-boiling point separation column 400 and the solvent separation column 500 is higher, energy costs and time for separation are increased.

In this regard, in the present invention, a settling tank 300 for removing the polymer in the reaction product is provided, thereby reducing energy costs used for separation in the high-boiling point separation column 400 and the solvent separation column 500 and shortening time, and thus, the problems described above were solved. Besides, an upper layer liquid stream having a high content of a solvent in the settling tank 300 is supplied directly to the solvent separation column 500 without passing through the high-boiling point separation column 400, thereby lowering a flow rate supplied to the high-boiling point separation column 400 to further reduce an energy use in the high-boiling point separation column 400.

The monomer stream may be supplied to the reactor 100 through a monomer stream supply line provided in a lower portion of the reactor 100. Here, the monomer may be supplied in a gaseous state to the reactor 100.

Specifically, the monomer stream including a gaseous monomer may be supplied to the reactor 100, and the gaseous monomer may be dissolved in a solvent supplied to the reactor 100 to carry out the oligomerization reaction in a liquid phase.

The monomer stream may be supplied from a naphtha cracking center (NCC). In the naphtha cracking center, a process including: introducing each of naphtha, C2 and C3 hydrocarbon compounds, propane, and the like to a supply raw material and carrying out cracking in each pyrolysis furnace; cooling cracking gas which has been pyrolyzed in each pyrolysis furnace to include hydrogen, and C1, C2, and C3 or higher hydrocarbon compounds; compressing the cooled cracking gas; and purifying a cracking compression stream including hydrogen, and C1, C2, and C3 or higher hydrocarbon compounds, may be carried out. Here, the monomer stream may be a stream including an ethylene monomer (C2) separated from naphtha cracking.

The solvent stream may be supplied to the reactor 100 through a solvent stream supply line provided in a lower side of the reactor 100. The solvent may include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. The solvent may be used in combination of two or more of the above materials, if necessary. Thus, a gaseous ethylene monomer may be liquefied at a higher temperature and a dissolution rate at which the gaseous ethylene monomer is dissolved in the solvent may be improved.

For example, the oligomerization reaction may be carried out under a pressure of 10 bar.g to 70 bar.g, 20 bar.g to 65 bar.g, or 20 bar.g to 40 bar.g. When ethylene is oligomerized within the temperature range and the pressure range, a selectivity to a desired α-olefin may be excellent, a by-product amount may be decreased, an operational efficiency of a continuous process may be increased, and costs may be reduced.

By-products produced in the oligomerization reaction in the reactor 100, for example, a polymer may be included at a content of 0.1 wt % to 5 wt %, 0.1 wt % to 4 wt %, or 1 wt % to 3 wt % in a discharge stream of the reactor 100.

The discharge stream of the reactor 100 may include a liquid first stream and a gaseous second stream. For example, in the reactor 100, a liquid reaction product including a desired oligomer product by the oligomerization reaction may be discharged through a product discharge line provided in a spaced state in a direction opposite to a lower side of the reactor 100, for example, a lower side of the reactor 100 where the solvent supply line is formed, as the first stream. For example, the product discharge line may be formed at the same height as the solvent supply line. In addition, the product discharge line of the reactor 100 is connected to a separation device 200 and may transfer a reaction product to the separation device 200.

In addition, the second stream including a gaseous unreacted monomer which is not dissolved in a solvent and does not participate in the oligomerization reaction may be discharged through an unreacted monomer discharge line provided in an upper portion of the reactor 100. For example, the gaseous second stream passes through a condenser 110 and is condensed into a liquid phase, and may be supplied to the separation device 200 with the first stream. Here, the first stream and the second stream may be supplied to the separation device 200 through a separate line or may be joined as one line and supplied to the separation device 200.

According to an exemplary embodiment of the present invention, the discharge stream of the reactor 100 is supplied to the separation device 200 in which the unreacted monomer in the reaction product may be separated. Specifically, in the separation device 200, the unreacted monomer is separated as an upper discharge stream from the discharge stream of the reactor 100 including the reaction product supplied and is circulated to the reactor 100 for reuse. Here, the upper discharge stream of the separation device 200 may pass through the compressor 210 for securing flowability to the reactor 100 and be circulated to the reactor 100. In addition, the lower discharge stream of the separation device 200 may be supplied as the reaction product from which most unreacted monomers are removed to a settling tank 300.

An operation temperature and an operation pressure of the separation device 200 may be controlled for selectively separating the unreacted monomer, for example, a low-boiling point material including monomers and dimers to the upper portion. For example, the operation temperature of the separation device 200 may be 20° C. to 250° C., 30° C. to 200° C., or 40° C. to 160° C., and the operation pressure of the separation device 200 may be 10 bar.g to 30 bar.g, 10 bar.g to 25 bar.g, or 10 bar.g to 20 bar.g.

According to an exemplary embodiment of the present invention, the lower discharge stream of the separation device 200 is supplied to the settling tank 300, and the polymer in the reaction product may be removed in the settling tank 300. Specifically, in the settling tank 300, the polymer floating in the reaction polymer may settle and be discharged to a lower portion of the settling tank 300 to be removed.

An internal temperature and an internal pressure of the settling tank 300 may be controlled for settling and removing the polymer in the reaction product. For example, the internal temperature of the settling tank 300 may be controlled to 10° C. to 90° C., 10° C. to 85° C., or 20° C. to 80° C., and the internal pressure of the settling tank 300 may be controlled to 0.1 $kg/cm^2$ to 3 $kg/cm^2$, 0.5 $kg/cm^2$ to 2 $kg/cm^2$, or 0.5 $kg/cm^2$ to 1.5 $kg/cm^2$. Here, the internal pressure of the settling tank 300 may be controlled using an inert gas. The inert gas may include one or more selected from the group consisting of nitrogen ($N_2$) and argon (Ar), and as a specific example, the inert gas may be nitrogen ($N_2$).

In addition, the settling tank 300 may control a residence time for settling and removing the polymer in the reaction product. For example, the lower discharge stream of the separation device 200 is supplied to the settling tank 300, and the residence time in the settling tank 300 may be 2 hours or more, 2 hours to 10 hours, or 2 hours to 6 hours.

As such, the internal temperature, the internal pressure, and the residence time in the settling tank 300 are controlled as described above, thereby effectively settling the polymer included in the lower discharge stream of the separation device 200 and removing the polymer. Here, the polymer may have a weight average molecular weight of 80,000 g/mol to 300,000 g/mol, 100,000 g/mol to 200,000 g/mol, or 100,000 g/mol to 150,000 g/mol.

Also, in the process of controlling the internal temperature, the internal pressure, and the residence time in the settling tank 300 to remove the polymer, layer separation into an upper layer liquid having a high content of the solvent and a lower layer liquid having a high content of the oligomer may be performed in the settling tank 300. The upper layer liquid separated in the settling tank 300, which has a high content of a solvent and contains almost no impurities other than the solvent, is not supplied to a high-boiling point separation column 400, but is directly supplied to a solvent separation column 500. Here, the content of the solvent in the upper layer liquid in the settling tank 300 may be 90 wt % or more, 90 wt % to 100 wt %, or 95 wt % to 100 wt %. As such, in the settling tank 300, the polymer is removed while the upper layer liquid containing almost no impurities other than the solvent is directly supplied to the solvent separation column 500 without passing through the high-boiling point separation column 400, thereby a flow rate supplied to the high-boiling point separation column 400 is decreased to reduce energy costs for separation in the high-boiling point separation column 400.

The upper layer liquid and the lower layer liquid which are layer-separated in the settling tank 300 may be different depending on the contents of the solvent and the oligomer included in the lower discharge stream of the separation device 200, and in order to supply an upper layer liquid stream to the solvent separation column 500, a solvent extraction line 310 provided to be connected from the solvent separation column 500 and extended to an area where the upper layer liquid in the settling tank 300 is formed may be further provided. Here, a pump 320 is installed in an arbitrary area of the solvent extraction line 310 to transfer the upper layer liquid stream of the settling tank 300 to the solvent separation column 500.

In addition, the lower layer liquid stream of the settling tank 300 has a high content of the oligomer and may be supplied to the high-boiling point separation column 400. Here, the content of the polymer in a lower layer liquid stream of the settling tank 300 may be 10 wt % or less, 0.1 wt % to 5 wt %, or 0.1 wt % to 5 wt %. In addition, a content ratio of the polymer in the lower layer liquid stream of the settling tank 300 to the polymer in the discharge stream of the reactor 100 may be 1:0.01 to 1:0.05, 1:0.01 to 1:0.04, or 1:0.01 to 1:0.03. This may mean that 95% or more of the polymer included in the discharge stream of the reactor 100 is removed from the settling tank 300, from which it is seen that energy costs required in the separation in the solvent separation column 500 with the high-boiling point separation column 400 may be reduced and a time therefor may be shortened.

According to an exemplary embodiment of the present invention, the lower layer liquid stream of the settling tank 300 is supplied to the high-boiling point separation column 400 and the high-boiling point material included in the lower layer liquid stream of the settling tank 300 may be removed by distillation in the high-boiling point separation column 400. Here, since only the lower layer liquid of the settling tank 300 is supplied to the high-boiling point separation column 400, a flow rate supplied to the high-boiling point separation column 400 is decreased, and since the content of the polymer in the lower layer liquid is low, energy costs for separation in the high-boiling point separation column may be reduced and a period therefor may be shortened.

The high-boiling point material is removed from the lower discharge stream in the high-boiling point separation column 400, and the remaining components, that is, the upper discharge stream having a high content of the oligomer may be supplied to the solvent separation column 500 to purify the oligomer.

According to an exemplary embodiment of the present invention, the solvent and the oligomer may be separated by a boiling point difference between the solvent and the oligomer in the solvent separation column 500. Specifically, the upper layer liquid stream of the settling tank 300 and the upper discharge stream of the high-boiling point separation column 400 are supplied to the solvent separation column 500 and may be separated into the solvent and the oligomer in the solvent separation column 500. Here, when the oligomer includes two or more oligomers having different boiling points, two or more solvent separation column 500 may be provided. For example, when two or more having different boiling points are included, a high boiling point oligomer is separated in a first solvent separation column and the solvent and a low boiling point oligomer may be separated in a second solvent separation column.

A solvent stream separated from the solvent separation column 500 is discharged to a lower portion of the solvent separation column 500, which may be circulated to the reactor 100 and reused. Thus, raw material costs may be reduced to lower a unit cost of the oligomer product to secure competitiveness.

According to an exemplary embodiment of the present invention, devices required for oligomer production, such as a valve, a condenser, a reboiler, a pump, a separation device, a compressor, and a mixer may be further installed in the method of producing an oligomer.

Hereinabove, the method of producing an oligomer according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated separately may be appropriately applied and used for carrying out the method of producing an oligomer according to the present invention.

Hereinafter, the present invention will be described in more detail by the Examples. However, the following Examples are provided for illustrating the present invention, and it is apparent to a person skilled in the art that various modifications and alterations may be made without departing from the scope and spirit of the present invention and the scope of the present invention is not limited thereto.

EXAMPLES

Example 1

An α-olefin was produced according to the process flow diagram illustrated in FIG. 1.

Specifically, a gaseous ethylene monomer stream was supplied to a lower portion of the reactor 100, methylcyclohexane was supplied to a lower side thereof, and a catalyst and a cocatalyst were supplied thereto, thereby performing an oligomerization reaction of an ethylene monomer to produce a reaction product including an α-olefin as an oligomer. Here, a content of a polymer included in the reaction product was confirmed to be 1.9 wt %.

A discharge stream of the reactor 100 was supplied to a separation device 200. Specifically, a gaseous second stream was condensed into a liquid phase by a condenser 110 and then supplied to the separation device 200, and a liquid first stream was directly supplied to the separation device 200.

An upper discharge stream of the separation device 200 including a gaseous unreacted monomer passed through a compressor 210 and was supplied to the reactor 100, and a lower discharge stream was supplied to a settling tank 300.

In the settling tank 300, an internal temperature of the lower discharge stream of the separation device 200 supplied was controlled to 40° C., and the stream resided for 4 hours in a state of supplying nitrogen ($N_2$) to control the internal pressure to 1 kg/cm$^2$ to perform layer separation. Here, the settled polymer was discharged to a lower portion to be removed and an upper layer liquid and a lower layer liquid were supplied to a high-boiling point separation column 400 at a flow rate of 8.0 kg/hr. Here, it was confirmed that a content of the solvent in the upper layer liquid was 98 wt % and a content of the polymer in the lower layer liquid was 0.7 wt %.

In the high-boiling point separation column 400, a high-boiling point material was removed in a lower portion and an upper discharge stream was supplied to a solvent separation column 500. Here, an energy use in the high-boiling point separation column 400 was confirmed to be 2,480 kcal/hr.

In the solvent separation column 500, α-olefin was recovered as an oligomer in a side portion and a lower discharge stream was circulated to the reactor 100. Here, it was confirmed that an energy use in the solvent separation column 500 was 2,430 kcal/hr.

Example 2

An α-olefin was produced according to the process flow diagram illustrated in FIG. 2.

Specifically, a gaseous ethylene monomer stream was supplied to a lower portion of the reactor 100, methylcyclohexane was supplied to a lower side thereof, and a catalyst and a cocatalyst were supplied thereto, thereby performing an oligomerization reaction of an ethylene monomer to produce a reaction product including an α-olefin as an oligomer. Here, a content of a polymer included in the reaction product was confirmed to be 1.9 wt %.

A discharge stream of the reactor 100 was supplied to the separation device 200. Specifically, a gaseous second stream was condensed into a liquid phase by the condenser 110 and then supplied to the separation device 200, and a liquid first stream was directly supplied to the separation device 200.

An upper discharge stream of the separation device 200 including a gaseous unreacted monomer passed through the compressor 210 and was supplied to the reactor 100, and a lower discharge stream was supplied to the settling tank 300.

In the settling tank 300, an internal temperature of the lower discharge stream of the separation device 200 supplied was controlled to 20° C., and the stream resided for 2 hours in a state of supplying nitrogen ($N_2$) to control the internal pressure to 1 kg/cm$^2$ to perform layer separation. Here, the settled polymer was discharged to a lower portion to be removed, an upper layer liquid having a content of the solvent of 97 wt % was supplied to the solvent separation column 500 using a pump 320 through a solvent extraction line 310 at a flow rate of 3.0 kg/hr, and a lower layer liquid having a content of the polymer of 0.25 wt % was supplied to the high-boiling point separation column 400 at a flow rate of 3.5 kg/hr.

In the high-boiling point separation column 400, a high-boiling point material was removed in a lower portion and an upper discharge stream was supplied to the solvent separation column 500. Here, an energy use in the high-boiling point separation column 400 was confirmed to be 2,200 kcal/hr.

In the solvent separation column 500, α-olefin was recovered as an oligomer in a side portion and a lower discharge stream was circulated to the reactor 100. Here, it was confirmed that an energy use in the solvent separation column 500 was 2,400 kcal/hr.

Example 3

The process was performed in the same manner as in Example 2, except that the internal temperature of the settling tank 300 was controlled to 40° C.

Here, in the settling tank 300, the settled polymer was discharged to a lower portion to be removed, an upper layer liquid having a content of the solvent of 95 wt % was supplied to the solvent separation column 500 using a pump 320 through a solvent extraction line 310 at a flow rate of 3.0 kg/hr, and a lower layer liquid having a content of the polymer of 0.34 wt % was supplied to the high-boiling point separation column 400 at a flow rate of 3.5 kg/hr.

In addition, it was confirmed that an energy use in the high-boiling point separation column 400 was 2,050 kcal/hr and an energy use in the solvent separation column 500 was 2,350 kcal/hr.

Example 4

The process was performed in the same manner as in Example 2, except that the internal temperature of the settling tank 300 was controlled to 80° C.

Here, in the settling tank 300, the settled polymer was discharged to a lower portion to be removed, an upper layer liquid having a content of the solvent of 92 wt % was supplied to the solvent separation column 500 using a pump 320 through a solvent extraction line 310 at a flow rate of 3.0 kg/hr, and a lower layer liquid having a content of the polymer of 0.43 wt % was supplied to the high-boiling point separation column 400 at a flow rate of 3.5 kg/hr. In addition, it was confirmed that an energy use in the high-boiling point separation column 400 was 2,030 kcal/hr and an energy use in the solvent separation column 500 was 2,370 kcal/hr.

Example 5

The process was performed in the same manner as in Example 3, except that the residence time in the settling tank 300 was controlled to 4 hours.

Here, in the settling tank 300, the settled polymer was discharged to a lower portion to be removed, an upper layer liquid having a content of the solvent of 98 wt % was supplied to the solvent separation column 500 using a pump 320 through a solvent extraction line 310 at a flow rate of 3.0 kg/hr, and a lower layer liquid having a content of the polymer of 0.21 wt % was supplied to the high-boiling point separation column 400 at a flow rate of 3.5 kg/hr.

In addition, it was confirmed that an energy use in the high-boiling point separation column 400 was 2,100 kcal/hr and an energy use in the solvent separation column 500 was 2,350 kcal/hr.

Example 6

The process was performed in the same manner as in Example 3, except that the residence time in the settling tank 300 was controlled to 6 hours.

Here, in the settling tank 300, the settled polymer was discharged to a lower portion to be removed, an upper layer liquid having a content of the solvent of 99 wt % was supplied to the solvent separation column 500 using a pump 320 through a solvent extraction line 310 at a flow rate of 3.0 kg/hr, and a lower layer liquid having a content of the polymer of 0.18 wt % was supplied to the high-boiling point separation column 400 at a flow rate of 3.5 kg/hr.

In addition, it was confirmed that an energy use in the high-boiling point separation column 400 was 2,050 kcal/hr and an energy use in the solvent separation column 500 was 2,330 kcal/hr.

It was confirmed that in Examples 1 to 6, the lower discharge stream of the separation device 200 was supplied to the settling tank 300 to remove the polymer before being supplied to the high-boiling point separation column 400, thereby reducing energy used in the high-boiling point separation column 400 and the solvent separation column 500 at a rear end.

In particular, in Examples 2 to 6 in which in the settling tank 300, the upper layer liquid was not supplied to the high-boiling point separation column 400 with the lower layer liquid, but was separately supplied to the solvent separation column 500 using the pump 320 through the solvent extraction line 310, it was confirmed that an energy reduction effect was larger.

COMPARATIVE EXAMPLE

Comparative Example 1

An α-olefin was produced according to the process flow diagram illustrated in FIG. 3.

Specifically, a gaseous ethylene monomer stream was supplied to a lower portion of the reactor 100, methylcyclohexane was supplied to a lower side thereof, and a catalyst and a cocatalyst were supplied thereto, thereby performing an oligomerization reaction of an ethylene monomer to produce a reaction product including an α-olefin as an oligomer. Here, a content of a polymer included in the reaction product was confirmed to be 1.9 wt %.

A discharge stream of the reactor 100 was supplied to the separation device 200. Specifically, a gaseous second stream was condensed into a liquid phase by the condenser 110 and then supplied to the separation device 200, and a liquid first stream was directly supplied to the separation device 200.

The upper discharge stream of the separation device 200 including a gaseous unreacted monomer passed through a compressor 210 and was supplied to the reactor 100, and a lower discharge stream having a content of the polymer of 2.2 wt % was supplied to the high-boiling point separation column 400 at a flow rate of 10 kg/hr.

In the high-boiling point separation column 400, a high-boiling point material was removed in a lower portion and an upper discharge stream was supplied to the solvent separation column 500. Here, an energy use in the high-boiling point separation column 400 was confirmed to be 3,800 kcal/hr.

In the solvent separation column 500, α-olefin was recovered as an oligomer in a side portion and a lower discharge stream was circulated to the reactor 100. Here, it was confirmed that an energy use in the solvent separation column 500 was 2,500 kcal/hr.

It was confirmed that in Comparative Example 1, a flow rate of the stream and a content of the polymer supplied to the high-boiling point separation column 400 were increased to increase an energy use in the high-boiling point separation column 400 and the solvent separation column 500 as compared with Examples 1 to 6.

The invention claimed is:

1. A method of producing an oligomer, the method comprising:
    supplying a monomer stream including a monomer and a solvent stream to a reactor to perform an oligomerization reaction using the monomer to produce a reaction product including an oligomer and a by-product, wherein the by-product comprises a polymer;
    supplying a discharge stream of the reactor to a separation device, and supplying an upper discharge stream of the separation device including an unreacted monomer to the reactor and supplying a lower discharge stream of the separation device to a settling tank;
    settling the polymer in the settling tank and removing the polymer, and supplying the lower discharge stream of the separation device from which the polymer is removed to a high-boiling point separation column;
    removing a high-boiling point material from a lower discharge stream of the high-boiling point separation column and supplying an upper discharge stream of the high-boiling point separation column including the oligomer to a solvent separation column; and
    separating a solvent and the oligomer in the solvent separation column,
    wherein layer separation into an upper layer liquid including the solvent and a lower layer liquid including the oligomer is performed in the settling tank, and an upper layer liquid stream is directly supplied to the solvent separation column and a lower layer liquid stream is supplied to the high-boiling point separation column.

2. The method of producing an oligomer of claim 1, wherein the discharge stream of the reactor includes a liquid first stream and a gaseous second stream, and the gaseous second stream passes through a condenser and is supplied to the separation device as a liquid phase with the liquid first stream.

3. The method of producing an oligomer of claim 1, wherein an internal temperature of the settling tank is 10° C. to 90° C., and an internal pressure of the settling tank is 0.1 kg/cm² to 3 kg/cm².

4. The method of producing an oligomer of claim 1, wherein a residence time of the lower discharge stream of the separation device in the settling tank is 2 hours or more.

5. The method of producing an oligomer of claim 1,
    wherein the upper layer liquid stream of the settling tank including the solvent is directly supplied to the solvent separation column through a solvent extraction line, and
    wherein the solvent extraction line connects the solvent separation column and an area where the upper layer liquid is formed in the settling tank.

6. The method of producing an oligomer of claim 1, wherein a content of the solvent in the upper layer liquid stream of the settling tank is 90 wt % or more.

7. The method of producing an oligomer of claim 1, wherein a content of the polymer in the lower layer liquid stream of the settling tank is 10 wt % or less.

8. The method of producing an oligomer of claim 1, wherein a content ratio of the polymer in the lower layer liquid stream of the settling tank to the polymer in the discharge stream of the reactor is 1:0.01 to 1:0.05.

9. The method of producing an oligomer of claim 1, wherein a solvent stream separated from the solvent separation column is supplied to the reactor.

10. The method of producing an oligomer of claim 1, wherein the monomer stream includes ethylene, the oligomer includes an α-olefin, and the polymer includes polyethylene.

\* \* \* \* \*